(12) United States Patent
Nakagawa et al.

(10) Patent No.: US 8,038,597 B2
(45) Date of Patent: Oct. 18, 2011

(54) INSTRUMENT FOR ENDOSCOPE

(75) Inventors: Tsuyoshi Nakagawa, Tokyo (JP); Yutaka Yanuma, Tokyo (JP); Yasushi Okoshi, Tokyo (JP); Isao Sasaki, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 56 days.

(21) Appl. No.: 11/479,492

(22) Filed: Jun. 30, 2006

(65) Prior Publication Data
US 2006/0247494 A1    Nov. 2, 2006

Related U.S. Application Data

(63) Continuation of application No. PCT/JP2005/008616, filed on May 11, 2005.

(30) Foreign Application Priority Data

May 13, 2004    (JP) ................................. 2004-143614
Apr. 11, 2005    (JP) ................................. 2005-113436

(51) Int. Cl.
*A61B 1/00*    (2006.01)
(52) U.S. Cl. .................... 600/104; 600/102; 600/153
(58) Field of Classification Search .............. 600/104, 600/153, 102, 106, 154, 131
See application file for complete search history.

(56) References Cited

U.S. PATENT DOCUMENTS

| | | | | |
|---|---|---|---|---|
| 4,960,411 A * | 10/1990 | Buchbinder | ............ | 604/95.01 |
| 5,059,177 A * | 10/1991 | Towne et al. | ............ | 604/102.02 |
| 5,323,768 A | 6/1994 | Saito et al. | | |
| 5,788,681 A | 8/1998 | Weaver et al. | | |
| 5,797,835 A * | 8/1998 | Green | ............ | 600/106 |
| 6,017,340 A | 1/2000 | Cassidy et al. | | |
| 6,071,233 A * | 6/2000 | Ishikawa et al. | ............ | 600/104 |
| 6,352,503 B1 * | 3/2002 | Matsui et al. | ............ | 600/104 |
| 2004/0015050 A1 | 1/2004 | Goto et al. | | |

FOREIGN PATENT DOCUMENTS

| | | |
|---|---|---|
| EP | 1 502 537 A1 | 2/2005 |
| JP | 3-195547 | 8/1991 |
| JP | 5-115492 | 5/1993 |
| JP | 2003-116777 | 4/2003 |
| JP | 2004-49891 | 2/2004 |
| JP | 2004-180996 | 7/2004 |

OTHER PUBLICATIONS

Supplementary European Search Report dated Aug. 4, 2010.

* cited by examiner

*Primary Examiner* — Linda Dvorak
*Assistant Examiner* — Alireza Nia
(74) *Attorney, Agent, or Firm* — Scully, Scott, Murphy & Presser, P.C.

(57) ABSTRACT

The instrument for an endoscope is an instrument for an endoscope is able to move reciprocally in the channel of the endoscope along a guide wire, and includes: a sheath portion having a guide lumen into which the guide wire is inserted and another lumen disposed along the guide lumen. The proximal end of the sheath portion is bifurcated into the first sheath portion having the guide lumen and the second sheath portion having the other lumen.

7 Claims, 23 Drawing Sheets

D-D

E-E

F-F

INSTRUMENT FOR ENDOSCOPE

PRIORITY CLAIM

This application is continuation application of a PCT Application No. PCT/JP2005/008616, filed on May 11, 2005, entitled "INSTRUMENT FOR ENDOSCOPE" whose priority is claimed on Japanese Patent Application No. 2004-143614 filed on May 13, 2004, and Japanese Patent Application No. 2005-113436 filed on Apr. 11, 2005. The contents of which are incorporated herein by reference.

BACKGROUND OF THE INVENTION

1. Field of the Invention

The present invention relates to an instrument for an endoscope.

2. Description of Related Art

In recent years, cases in which an endoscopy procedure is employed have increased for affections in the alimentary tract system, and the pancreatic and bile duct systems. Treatments of the pancreatic and bile duct systems employing current endoscopes include a treatment for therapy for taking out a gallstone existing in the bile duct, etc., by using a balloon and holding device in addition to a diagnostic treatment for endoscopically contrasting the pancreatic duct and the bile duct.

Also, with respect to an endoscopy procedure for the pancreatic duct, the bile duct and the hepatic duct, etc., the distal end of an insertion portion of an endoscope is inserted into the vicinity of papilla of the duct, and an instrument such as a papilotomy knife or balloon is inserted from the endoscope into the pancreatic duct or the bile duct, using a guide wire as a guide under X-ray fluoroscopy. In a case where the instrument is inserted through a channel provided at the insertion portion of the endoscope, the instrument is inserted while inserting a guide wire, which is inserted into the channel in advance, into a guide wire lumen secured at the insertion portion of the instrument.

It has been proposed that an instrument operating portion for carrying out operation of an instrument be connected to the vicinity of the forceps port of an endoscope and be fixed thereat so that, when operating an instrument such as a papilotomy knife, a balloon or the like the operator can carry out operation of the instrument alone along with the endoscope operation (for example, refer to Japanese Unexamined Patent Application, First Publication No. 2004-49891). Thereby, even where there is a lone operator, the operator is able to easily and quickly carry out endoscope operation and instrument operation.

SUMMARY OF THE INVENTION

The invention provides an instrument for an endoscope, which is able to move reciprocally in a channel of the endoscope along a guide wire, comprising a sheath portion having a guide lumen into which the guide wire is inserted and another lumen disposed along the guide lumen, wherein the proximal end of the sheath portion is bifurcated into a first sheath portion having the guide lumen and a second sheath portion having the another lumen.

It is preferable that the instrument for an endoscope according to the present invention further include an instrument distal end portion for carrying out treatment on a portion to be treated, connected to the distal end of the sheath portion; a first operating portion for inserting and pulling out the guide wire, connected to the proximal end of the first sheath portion; a second operating portion for operating the instrument distal end portion, connected to the proximal end of the second sheath portion; and a connection portion for detachably engaging and disengaging one of the first operating portion or the second operating portion in the endoscope; wherein the other of the first operating portion or the second operating portion is attachable to and detachable from the other one.

It is preferable that the instrument for an endoscope according to the invention further include a reinforcement portion for maintaining the rigidity of the second sheath portion roughly at the same rigidity as that of the first sheath portion in which the guide wire is inserted into the guide lumen, inserted into an insertion hole disposed in the second sheath portion along another lumen.

DESCRIPTION OF THE PREFERRED EMBODIMENTS

Figure 1:
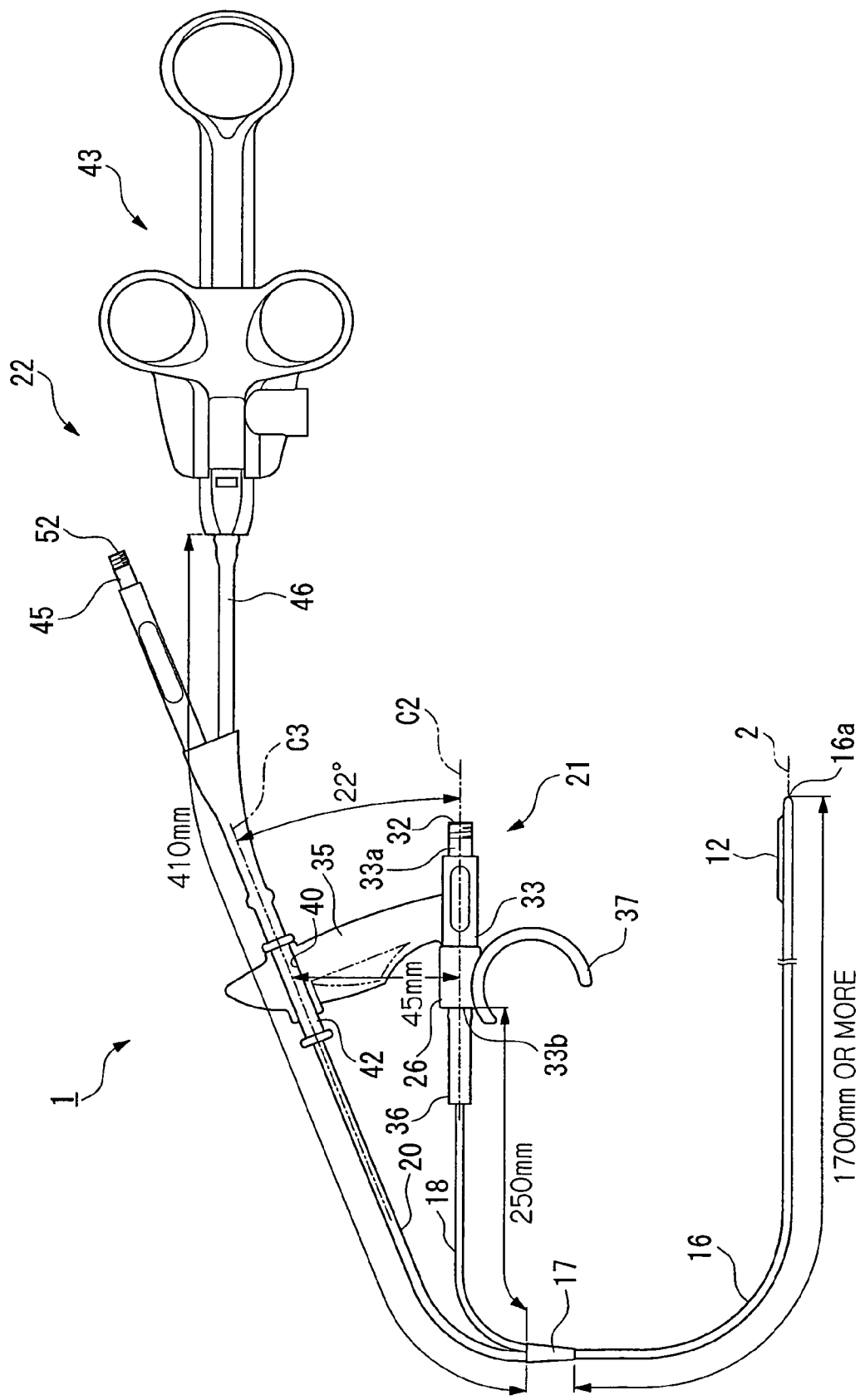
FIG. 1 is a plan view depicting a papilotomy knife according to Embodiment 1 of the invention.
Figure 2:
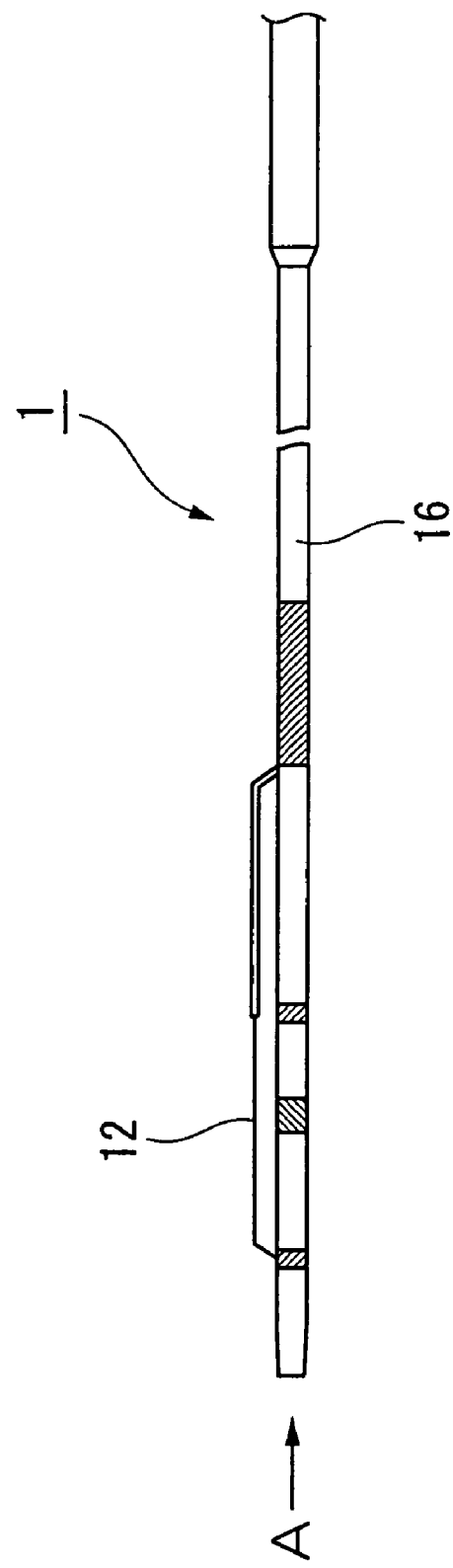
FIG. 2 is a plan view depicting the distal end of the papilotomy knife according to Embodiment 1 of the invention.
Figure 3:
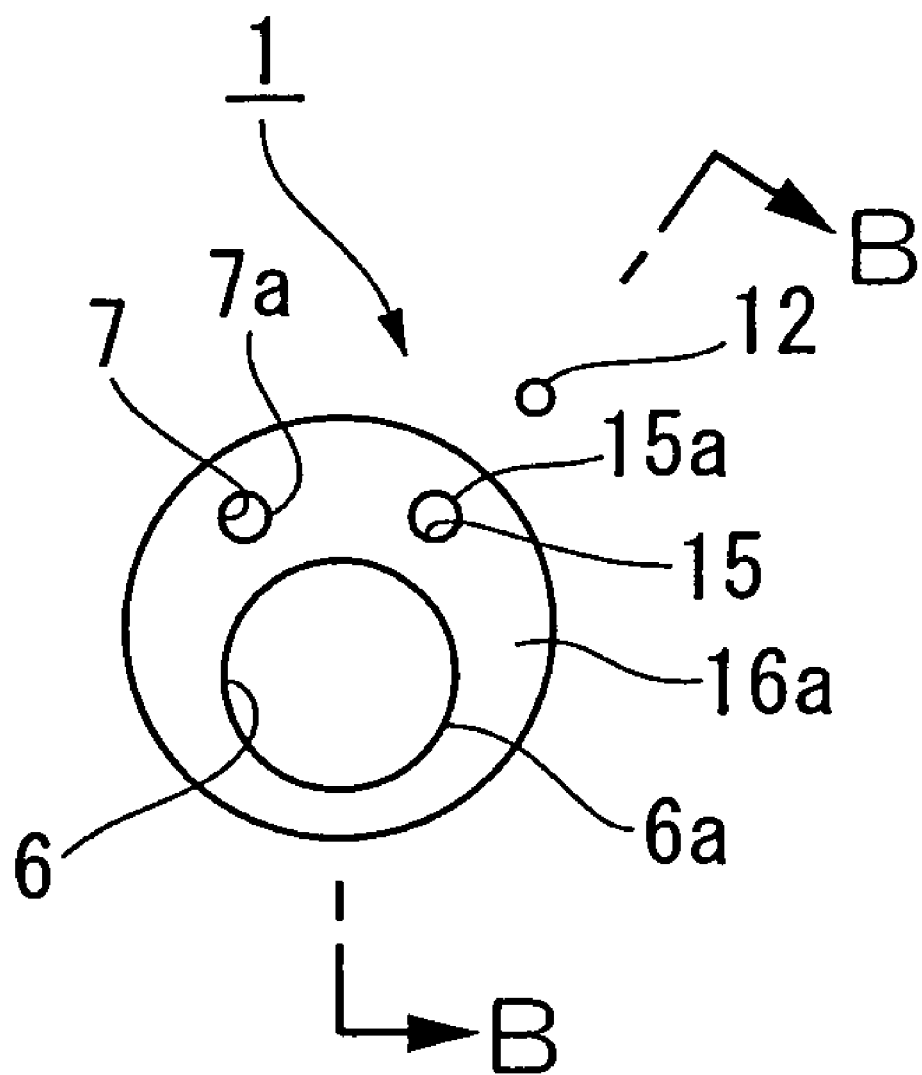
FIG. 3 is a view when looking in the direction of the arrow A of FIG. 2.
Figure 4:
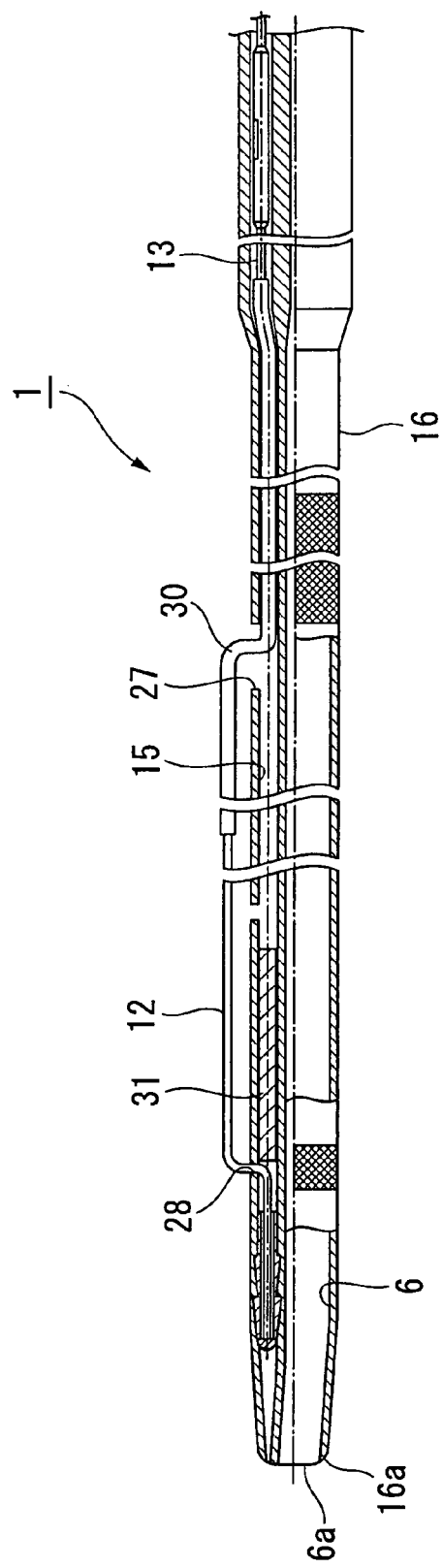
FIG. 4 is a sectional view taken along the line B-B of FIG. 3.

A description is given of Embodiment 1 of the invention with reference to FIG. 1 through FIG. 22.

A papilotomy knife (instrument for an endoscope) 1 according to the present embodiment is an instrument for an endoscope, which is able to move reciprocally in a channel 5 of an endoscope 3 along a guide wire 2. As depicted in FIG. 1 through FIG. 5, the papilotomy knife 1 includes a tube sheath (sheath portion) 16 having a guide lumen 6, a fluid-feeding lumen (another lumen) 7 and a wire lumen (still another lumen) 15. The guide wire 2 is inserted into the guide lumen 6. The fluid-feeding lumen 7 is disposed along the guide lumen 6, and a contrast medium can be fed thereinto. A wire portion 13 having a knife portion (instrument distal end portion) 12 connected to the distal end thereof is inserted into the wire lumen 15. The knife portion 12 incises, for example, a lesion, that is, a duodenal papilla (portion to be treated) 11 in a bile duct 8 or a pancreatic duct 10.

A tube sheath 16 is bifurcated into the first tube sheath 18 (the first sheath portion) and the second tube sheath (the second sheath portion) 20. The first tube sheath 18 includes a guide lumen 6 disposed at the proximal end side of the bifurcated portion 17. The second tube sheath 20 includes a fluid-feeding lumen 7 and a wire lumen 15.

Also, the papilotomy knife 1 includes the first operating portion 21, the second operating portion 22 and the first connection portion (connection portion) 26. The first operating portion 21 is connected to the proximal end of the first tube sheath 18, and operates the guide wire 2 to move reciprocally. The second operating portion 22 is connected to the proximal end of the second tube sheath 20, and operates the knife portion 12. The first connection portion 26 detachably engages the first operating portion 21 with the operating portion 25 of the endoscope 3 via an adapter 23. The second operating portion 25 is attachable to the first operating portion 21 and detachable therefrom.

The guide lumen 6, the fluid-feeding lumen 7 and the wire lumen 15 are disposed to run through the interior of the tube sheath 16. The distal end 6a of the guide lumen and the distal end 7a of the fluid-feeding lumen 7 opened at the distal end of the tube sheath 16.

The knife portion 12 protrudes to the outside of the tube sheath 16 from, and is again inserted into the wire lumen 15 from the second slit 28. The first slit 27 is formed on the outer wall at the distal end 16a side of the tube sheath 16 and communicating with the guide lumen 15, and the second slit 28 is formed on the outer wall at the distal end 16a side of the tube sheath 16 wit respect to the first slit 27. The distal end of the knife portion 12 is fixed at the distal end 15a side of the wire lumen 15.

The proximal end of the knife portion 12 is covered with an insulative tube sheath 30, which is electrically insulated, in order to prevent high-frequency power from flowing from the knife portion 12 to the endoscope 3 when it is supplied. A contrasting chip 31 for checking the position of the knife portion 12 by X-ray imaging is disposed at the wire lumen 15 at the portion where the knife portion 12 is exposed to the outside of the tube sheath 16.

Figure 6:
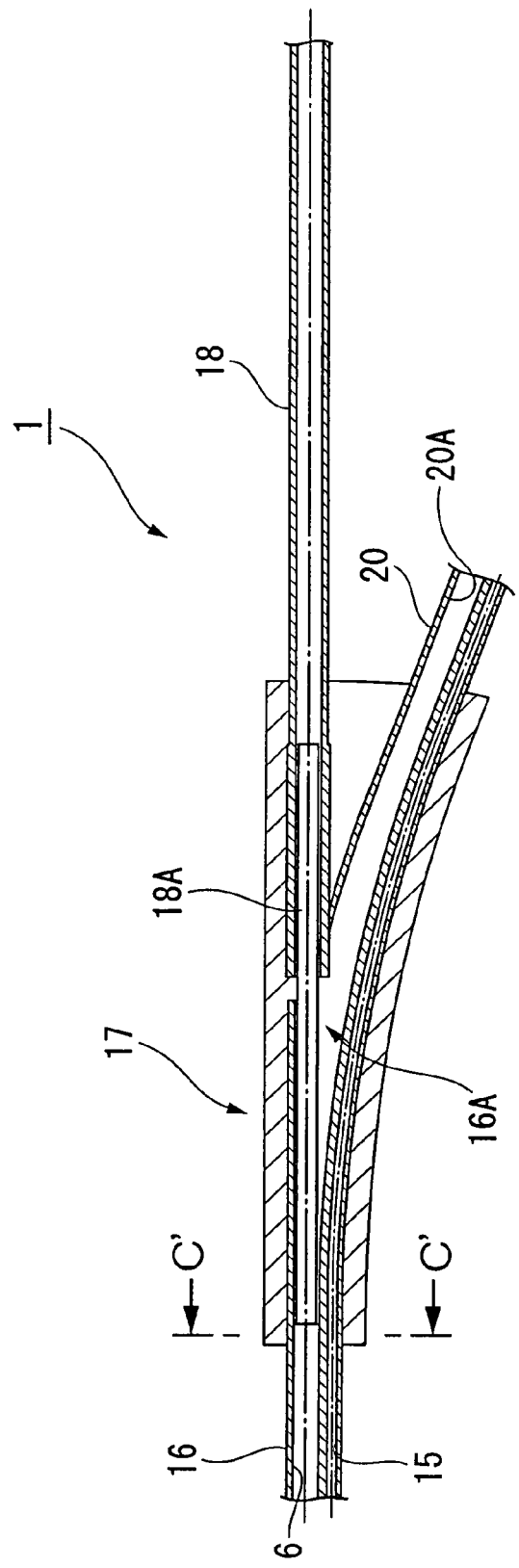
FIG. 6 is a cross-sectional view (cross-sectional view taken along the line C-C of FIG. 7) depicting a bifurcated portion of the papilotomy knife according to Embodiment 1 of the invention.
Figure 7:
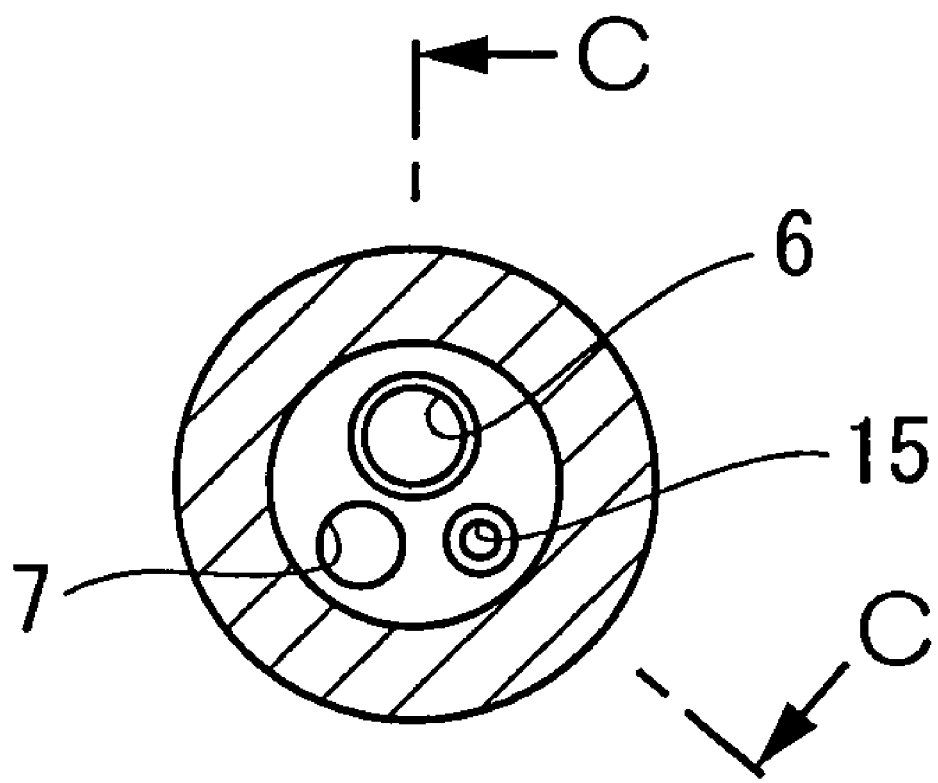
FIG. 7 is a cross-sectional view taken along the line C'-C' of FIG. 6.

As depicted in FIG. 6 and FIG. 7, a notch 16A is provided at the tube sheath 16 in the bifurcated portion 17. A reinforcement pipe 18A communicating with the guide lumen 6 is connected to the notch 16A, and the first tube sheath 18 is connected to a reinforcement pipe 18A. The tube sheath 16 positioned at the proximal end side from the bifurcated portion 17 and including the fluid-feeding lumen 7 and the wire lumen 15 is the second tube sheath 20.

The insertion hole 20A communicating with the notch 16A is disposed in the second tube sheath 20 along the fluid-feeding lumen 7 and the wire lumen 15.

The length between the distal end 16a of the tube sheath 16 and the bifurcated portion 17 is set to be 1700 mm or more.

Figure 8:
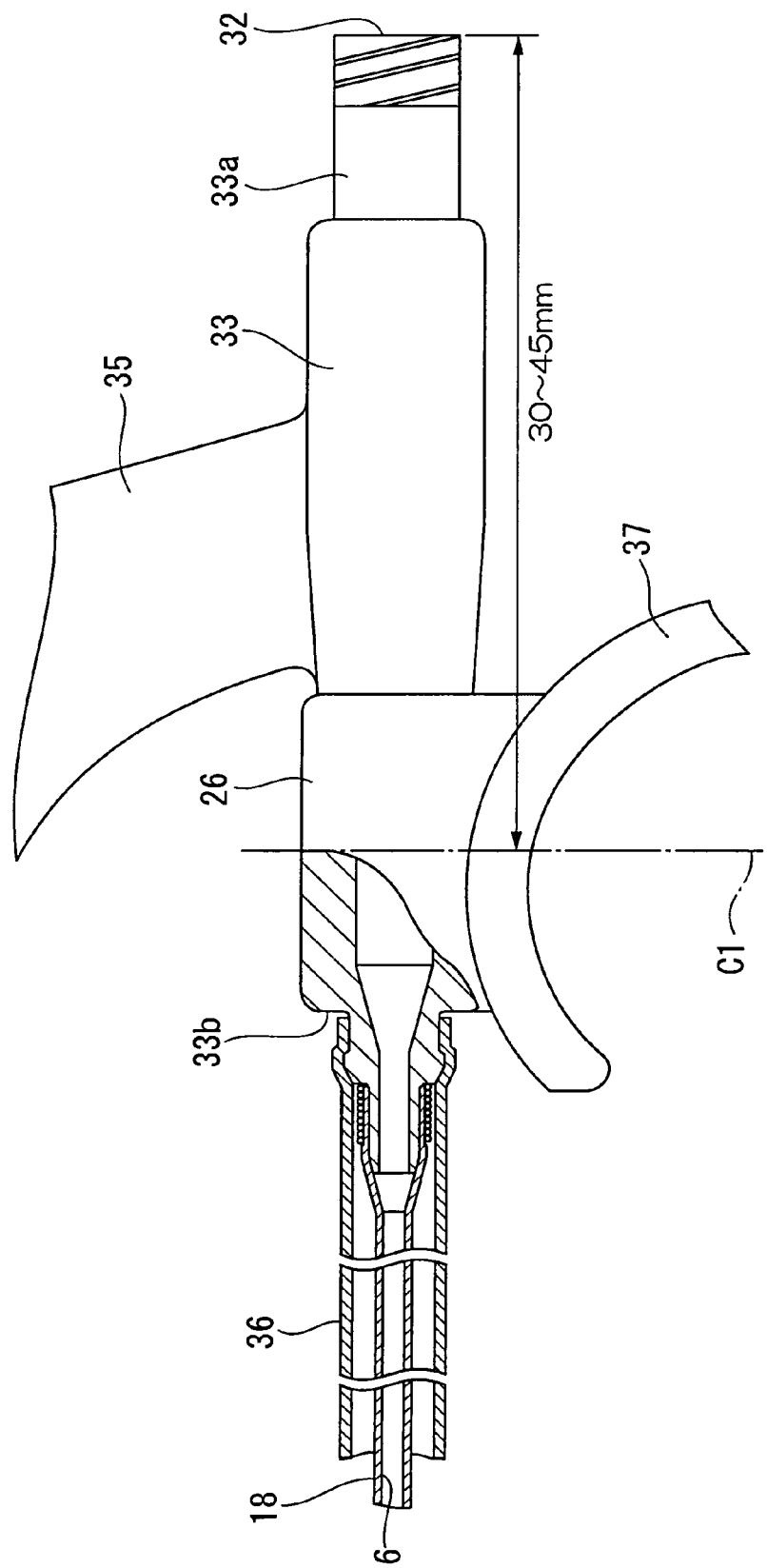
FIG. 8 is a magnified view depicting the major parts of the first operating portion of the papilotomy knife according to Embodiment 1 of the invention.
Figure 9:
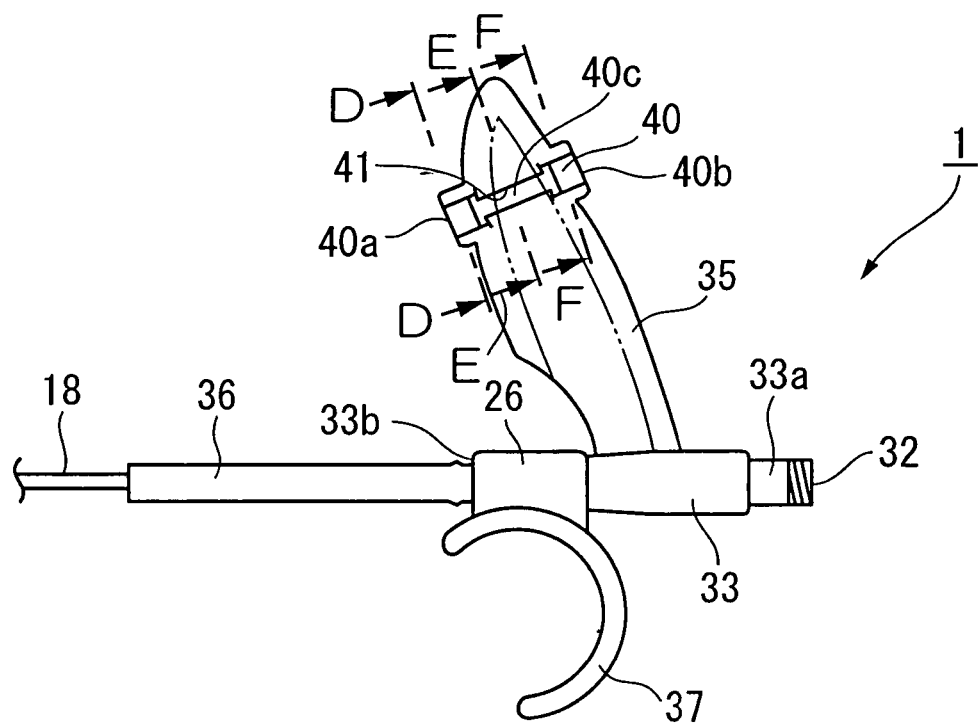
FIG. 9 is a side elevational view depicting the first operating portion of the papilotomy knife according to Embodiment 1 of the invention.
Figure 10:
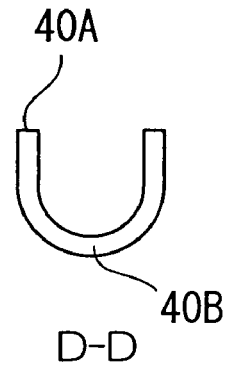
FIG. 10 is a cross-sectional view taken along the line D-D of FIG. 9.

As depicted in FIG. 8, the first operating portion 21 includes a guide wire insertion portion 33 and a second connection portion 35. The guide wire insertion portion 33 has a guide lumen inlet opening 32, into which the guide wire 2 is inserted, at one end 33a thereof, and is formed to be cylindrical so that the guide wire 2 is caused to run therethrough. The second connection portion 35 detachably connects the second operating portion 22 to the first operating portion 21.

The first tube sheath 18 is connected to the other end 33b of the guide wire insertion portion 33. The connection portion is covered by a reinforcement tube sheath 36 to prevent the first tube sheath from being folded.

As depicted in FIG. 8, the first connection portion 26 is disposed at the side face of the guide wire insertion portion 33. The distance between the attaching position C1 of the first connection portion 26 and the guide lumen inlet opening 32 is set to be 30 to 45 mm.

The first connection portion 26 is made of a resilient material, and is provided with a roughly cylindrically molded U-shaped portion 37 with a part thereof removed. The inner diameter of the U-shaped portion 37 is smaller than the outer diameter of a cylindrical portion 38 of the operating portion of the endoscope 3 or than the outer diameter of an cylindrical adapter portion 60, described later, of the adapter 23. Therefore, the U-shaped portion 37 is fitted to the cylindrical portion 38 or the cylindrical adapter portion 60 with the inner diameter thereof enlarged. At this time, since the U-shaped portion 37 exerts an elastic force by which it is restored to its shape, it is strongly fixed at the cylindrical portion 38 or the cylindrical adapter portion 60. The ridge lines of the U-shaped portion 37 are chamfered so as not to damage the cylindrical portion 38 and the cylindrical adapter portion 60.

The second connection portion 35 is disposed at the side opposite the side at which the U-shaped portion 37 is disposed, with the guide wire insertion portion 33 placed therebetween.

The length of the first tube sheath 18 from the bifurcated portion 17 to the attaching position of the first connection portion 26 is set to be 250 mm or more.

In the second connection portion 35, an engaging portion 40 is disposed at a position apart by 45 mm or more from the center axis C2 of the guide wire insertion portion 33. The engaging portion 40 can detachably mount a fixing portion 42 described later. The engaging portion 40 is formed to be grooved, wherein the center axis C3 and the center axis C2 of the guide wire insertion portion 33 forms an angle of almost 22 degrees.

Figure 11:
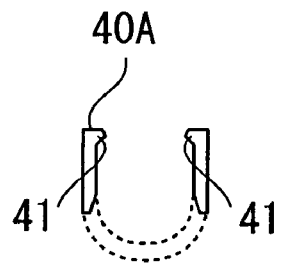
FIG. 11 is a cross-sectional view taken along the line E-E of FIG. 9.
Figure 12:
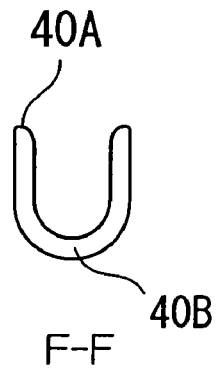
FIG. 12 is a cross-sectional view taken along the line F-F of FIG. 9.

As depicted in FIG. 9 through FIG. 12, one end 40a of the engaging portion 40 and the other end 40b thereof are provided with opening ends 40A having such a width that the fixing portion 42 can be fitted, and a bottom portion 40B, and are formed to be roughly U-shaped. The bottom portion 40B of the central portion 40C of the engaging portion 40 is made open, and, as depicted in FIG. 11, projection portions 41 protruding foward each other are formed at the inner faces, opposed to each other, of the opening ends 40A. The projection portions 41 are able to elastically deform. The engaging portion 40 has a depth such that the fixing portion 42 can be engaged and stopped between the projection portions 41 and the bottom portion 40B when the fixing portion 42 is fitted in the engaging portion 40.

The protrusion amount of the projection portions 41 and the opening width of the opening ends 40A are set so that the intensity of the fixing force required when the fixing portion 42 is engaged and held in the engaging portion 40 is made smaller than the intensity of the fixing force required when attaching the U-shaped portion 37 to the adapter 23 or the cylindrical portion 38 of the endoscope 3.

The second operating portion 22 includes a fixing portion 42, a knife operation handle 43, and a fluid-feeding portion 45. The fixing portion 42 is disposed at the proximal end of the second tube sheath 20 and is connectable to the first operating portion 21. The fixing portion 42 is composed of a material that is harder than the tube sheath 16, and is formed to be cylindrical so as to be engageable with the engaging portion 40.

Figure 13:
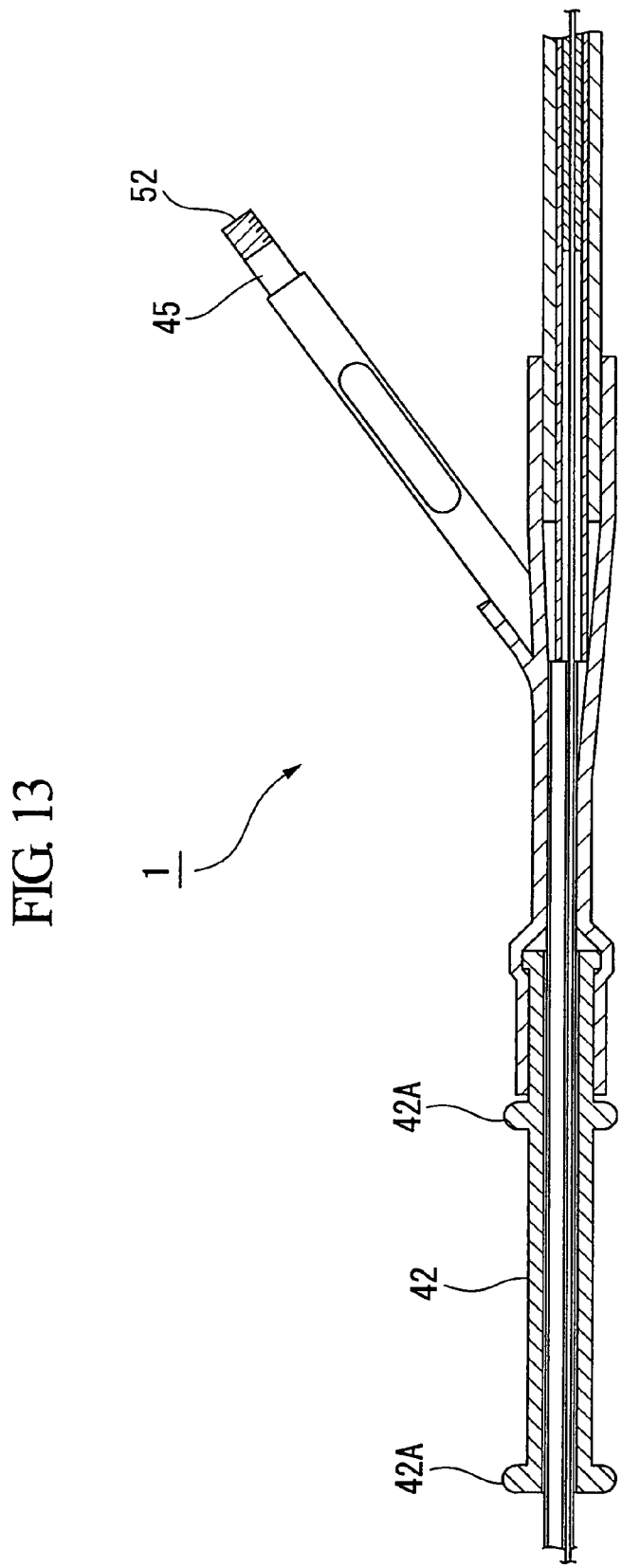
FIG. 13 is a cross-sectional view depicting a fixing portion of the papilotomy knife according to Embodiment 1 of the invention.

As depicted in FIG. 13, a diameter-enlarged portion 42A having a larger diameter than the width between the opening ends 40A is formed at both ends of the fixing portion 42 in order to regulate movement of the fixing portion 42 in the direction of the center axis C3 when the fixing portion 42 is engaged with the engaging portion 40.

The surface of the fixing portion 42 and the surface of the engaging portion 40 are given the same color so as to identify that these portions 42 and 40 can be mounted to each other.

Figure 14:
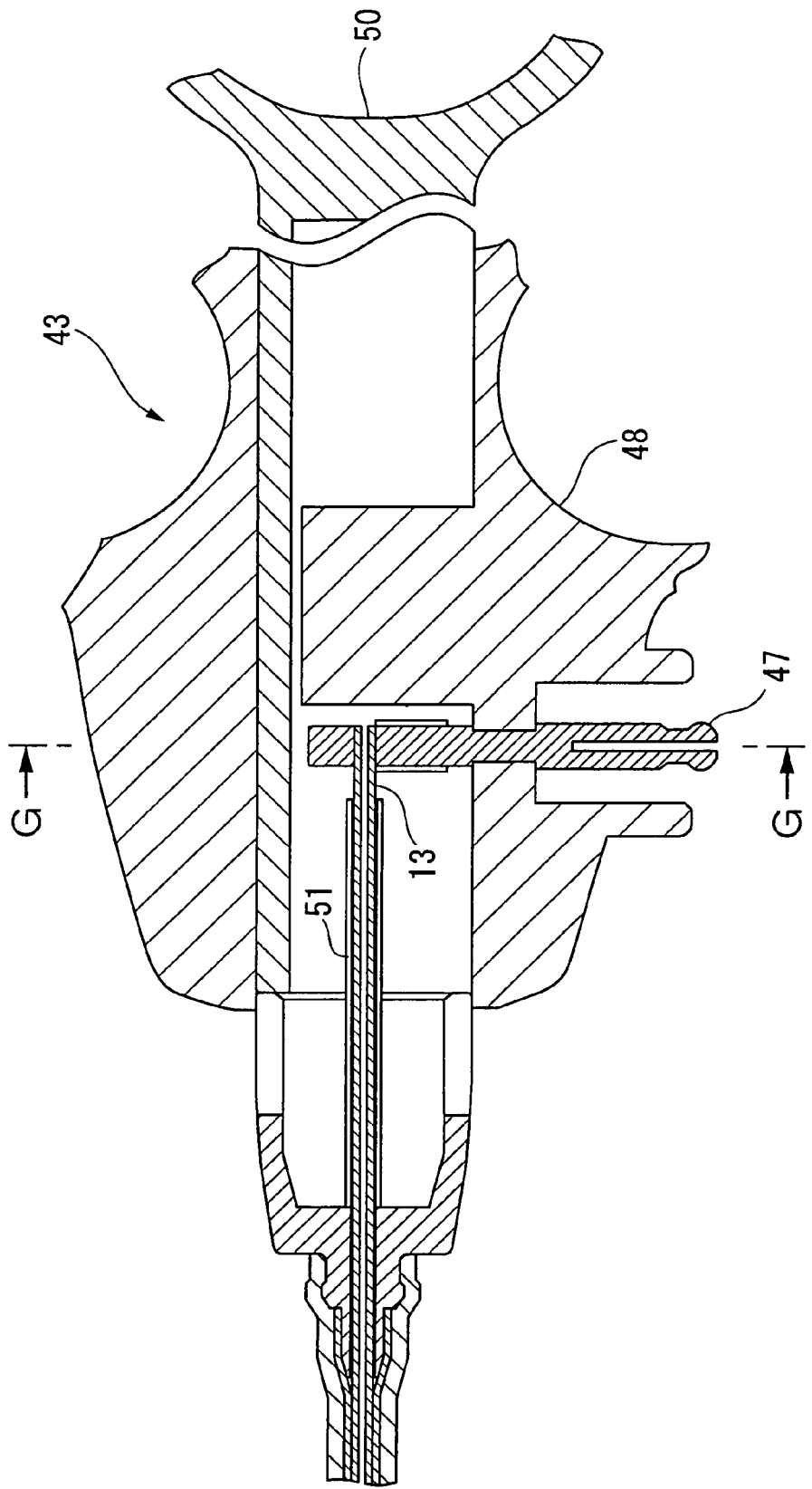
FIG. 14 is a magnified cross-sectional view depicting the second operating portion of the papilotomy knife according to Embodiment 1 of the invention.
Figure 15:
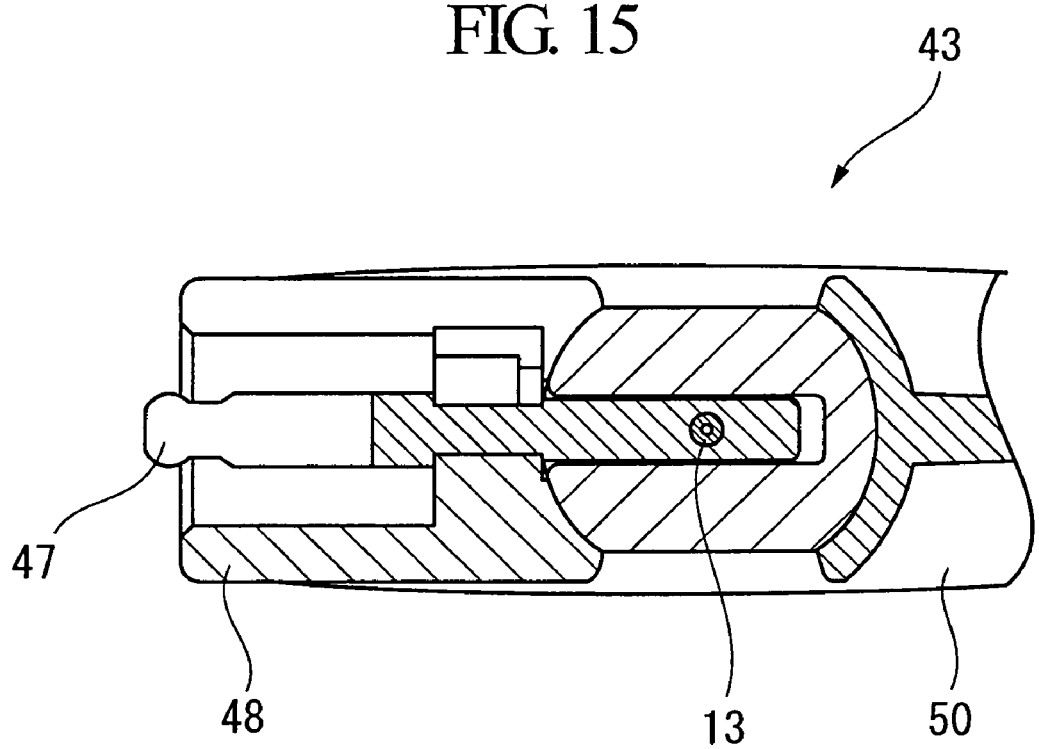
FIG. 15 is a cross-sectional view taken along the line G-G of FIG. 14.

The knife operation handle 43 operates the wire portion 13 to move reciprocally in the wire lumen 15. The knife operation handle 43 has the wire lumen 15, and is connected to the proximal end of a flexible wire tube sheath 46 bifurcated from the second tube sheath 20 at the fixing portion 42. As depicted in FIG. 14 and FIG. 15, the knife operation handle 43 has a terminal portion 47 connected to a high-frequency power source (not shown) and is provided with a slide portion 48 having the proximal end of the wire portion 13 connected thereto, and an operation main body 50 in which the slide portion 48 is disposed so as to move reciprocally therein.

The distance from the proximal end of the bifurcated portion 17 to the distal end of the operation main body 50 is set to a length of 410 mm. Also, the proximal end side of the wire portion 13 is covered by a stopper 51 and regulates a movement range of the slide portion 48.

A fluid feeding portion 45 is caused to communicate with the fluid-feeding lumen 7. The fluid-feeding portion 45 is formed to be cylindrical, wherein a fluid feeding mouthpiece 52 to which a syringe (not shown), etc., can be connected is disposed at the end portion thereof.

Figure 16:
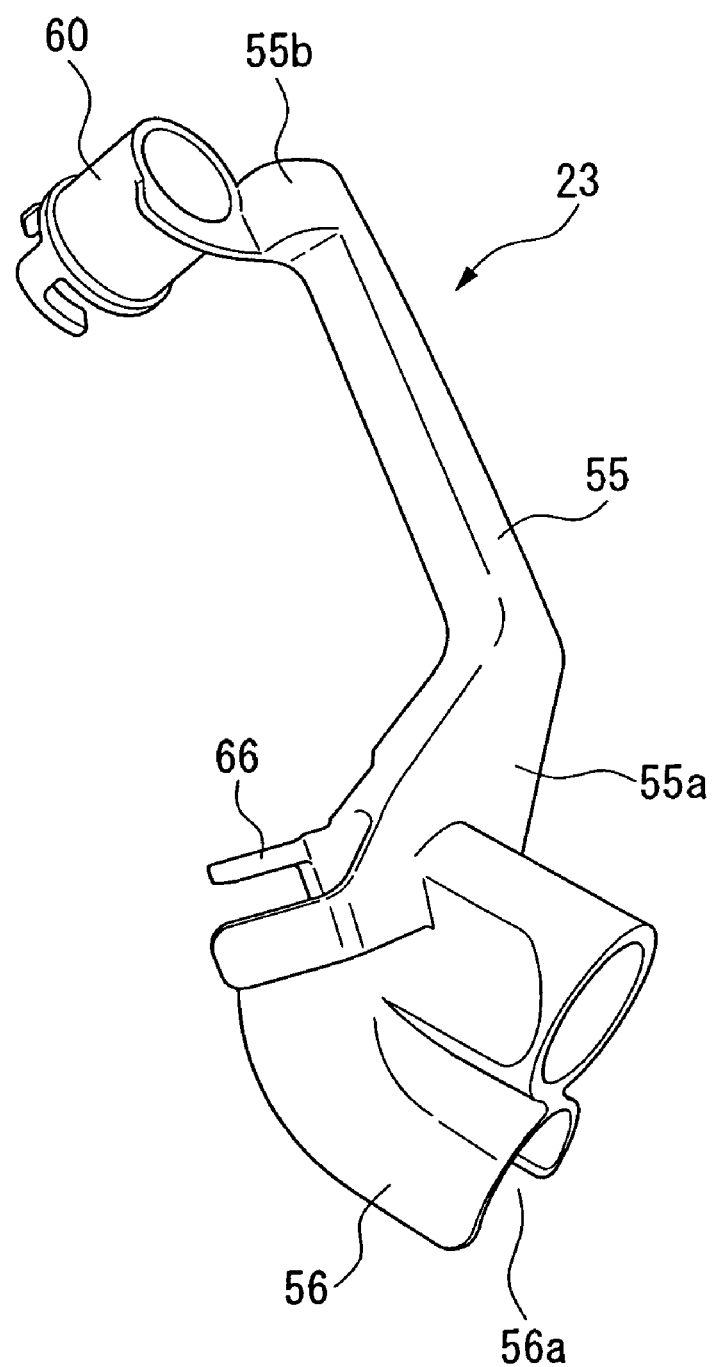
FIG. 16 is a perspective view depicting an adapter used when the papilotomy knife according to Embodiment 1 of the invention is mounted in an endoscope.

As depicted in FIG. 16, the adapter 23 includes a linkage portion 55, an endoscope fixing portion 56 and a cylindrical adapter portion 60.

Figure 17:
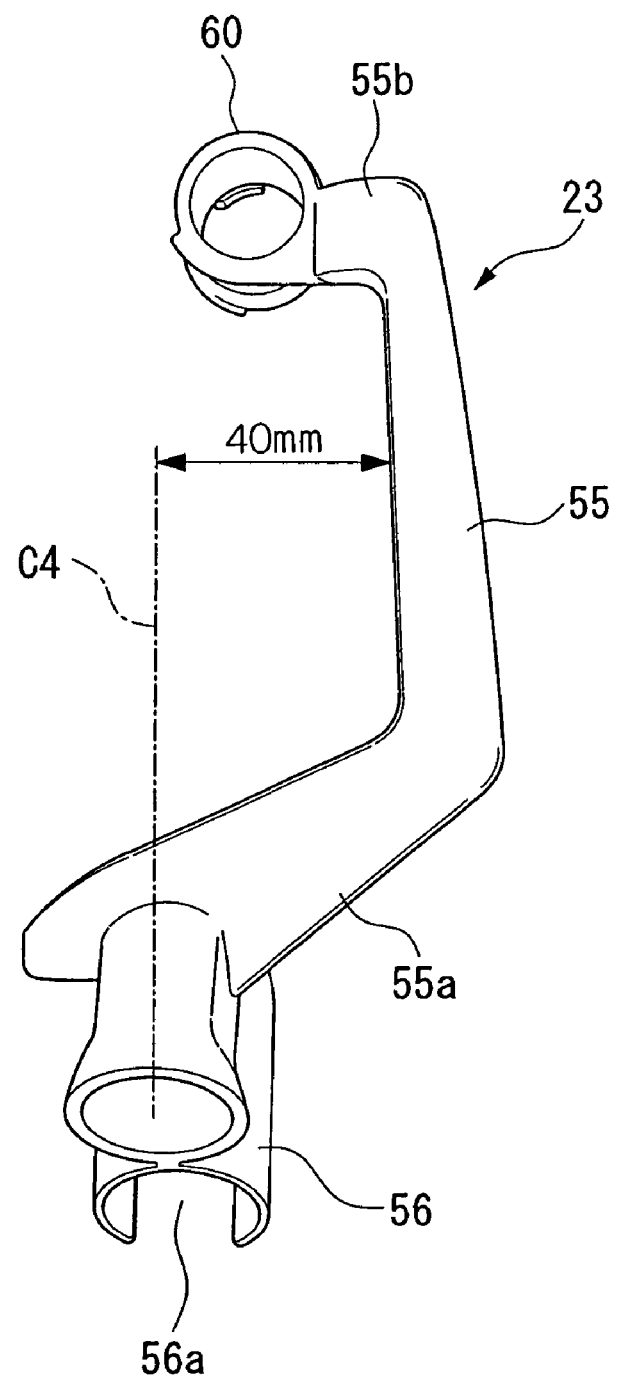
FIG. 17 is a plan view depicting an adapter used when the papilotomy knife according to Embodiment 1 of the invention is mounted in an endoscope.

The linkage portion 55 is formed to be rod-like, and, as depicted in FIG. 17, is disposed to be biased to a position apart by 40 mm from the center axis C4 of the endoscope fixing portion 56. The upper end portion 55b of the linkage portion 55 is curved in the direction of the center axis C4.

The endoscope fixing portion 56 is connected to the lower end portion 55a of the linkage portion 55 and is attachable to and detachable from the cylindrical portion 38 of the endoscope 3.

Figure 18:
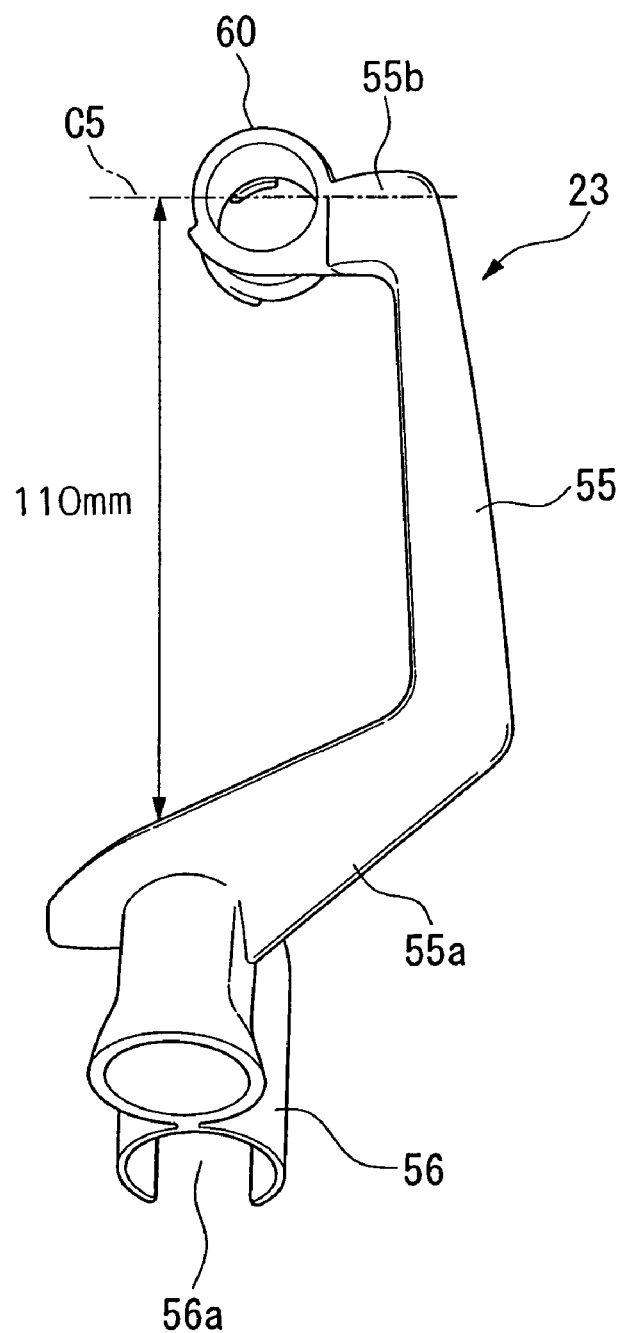
FIG. 18 is a plan view depicting an adapter used when the papilotomy knife according to Embodiment 1 of the invention is mounted in an endoscope.

The cylindrical adapter portion 60 is connected to the upper end portion 55b of the linkage portion 55 and allows the U-shaped portion 37 to be attached and detached. The center axis C5 of the cylindrical adapter portion 60 is disposed at a position apart by 110 mm from the endoscope fixing portion 56 as depicted in FIG. 18.

A regulation member 61 for positioning is disposed in the cylindrical adapter portion 60 in order to locate the guide wire 2 so that the wire 2 is not turned in the direction of an operator who operates the endoscope 3 from the guide lumen inlet opening 32 of the guide wire insertion portion 33 or in the direction of a patient. The regulation member 61 can stop and engage the end portion 37a of the U-shaped portion 37. Therefore, when the U-shaped portion 37 is mounted in the cylindrical adapter portion 60, the U-shaped portion 37 can slide by 90 degrees or more on the cylindrical adapter portion 60 until the end portion 37b is brought into contact with the regulation member 61.

Figure 19:
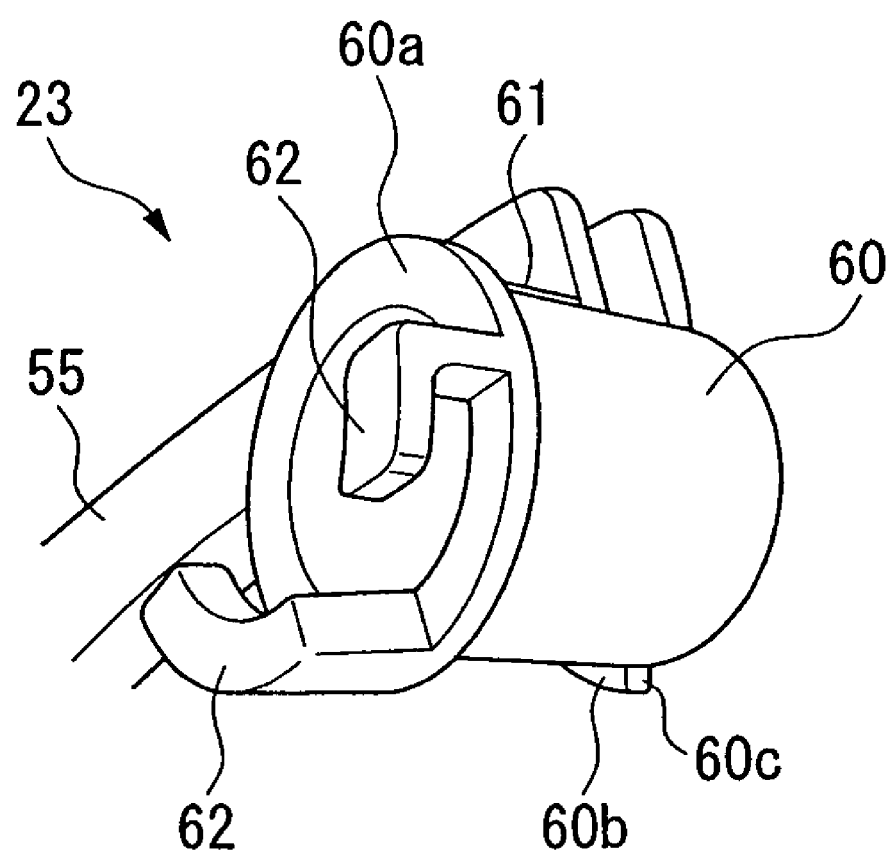
FIG. 19 is a magnified perspective view depicting the major parts of an adapter used when the papilotomy knife according to Embodiment 1 of the invention is mounted in an endoscope.

As depicted in FIG. 19, flange portions 60a and 60b are provided at both end sides of the cylindrical adapter portion 60 as depicted in FIG. 19. The flange portion 60b is partially provided with a notch 60c. The ridge lines of the flange portions 60a and 60b are chamfered to be round.

Two first hooks 62 protruding from the side face along the edge of the cylindrical adapter portion 60 are disposed on the end face at the flange portion 60a side of the cylindrical adapter portion 60. The first hooks 62 are disposed at positions where the tube sheath 16 or the guide wire 2 can be engaged and stopped so that the guide wire 2 is made roughly parallel to the tube sheath 16 inserted into a forceps plug 63 disposed in the endoscope 3 when the adapter 23 is mounted in the cylindrical portion 38.

Figure 20:
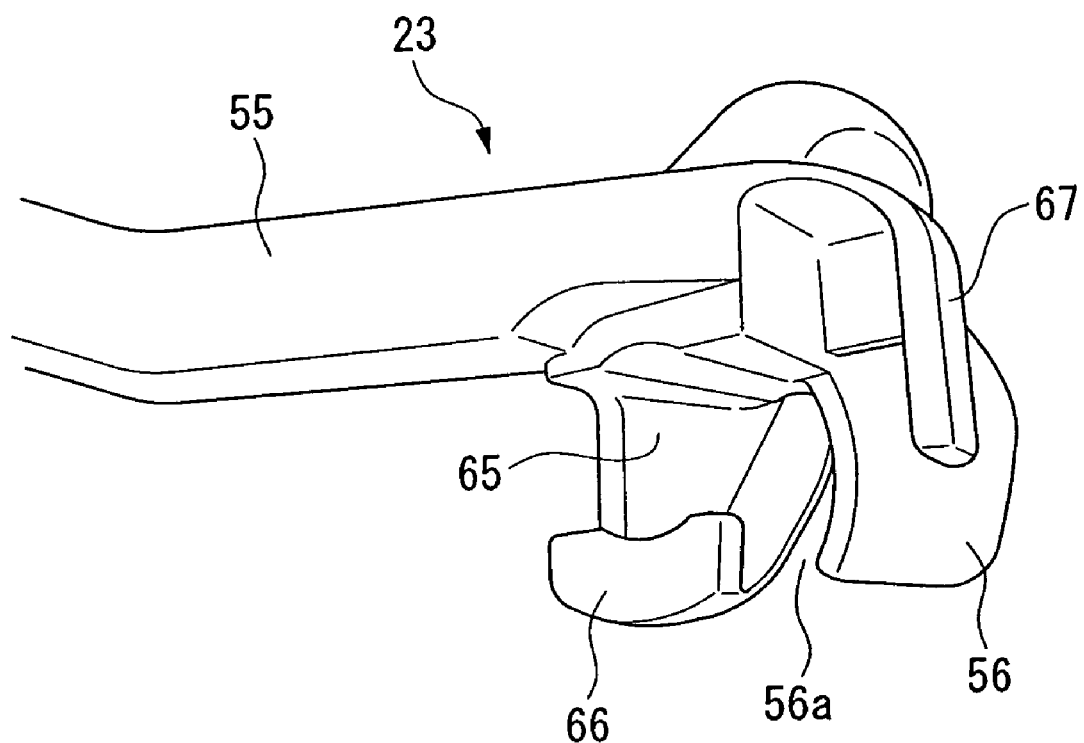
FIG. 20 is a magnified perspective view depicting the major parts of an adapter used when the papilotomy knife according to Embodiment 1 of the invention is mounted in an endoscope.

As depicted in FIG. 20, the endoscope fixing portion 56 has an inlet portion 56a and is made roughly semi-cylindrical so as to be mounted at the cylindrical portion 38. The ridge portion of the endoscope fixing portion 56 is chamfered to be round. A fitting portion 66 and a second hook 67 are provided in the vicinity of the endoscope fixing portion 56. The fitting portion 66 has a roughly U-shaped notch 65 as positioning means and is composed of a plate-shaped member engageable with the vicinity of the attaching portion of the forceps plug 63. The second hook 67 stops and engages the tube sheath 16 or the guide wire 2 in order to facilitate holding the tube sheath 16 and the guide wire 2 in a state where the direction of the guide wire 2 stopped and engaged at the first hook 62 is maintained.

Next, a description is given of a method for operating the papilotomy knife 1 according to the present embodiment, and of actions and effects thereof.

Here, it is assumed that the endoscope 3 is already inserted into a body cavity, the guide wire 2 is inserted from the forceps plug 63 to a desired position in the body cavity through the channel 5 by a known method and operations, and a predetermined treatment using the above-described instrument is carried out.

First, the adapter 23 is mounted at the operating portion 25 of the endoscope 3. That is, the inlet portion 56a of the endoscope fixing portion 56 is pushed along the lateral direction and is fitted to the cylindrical portion 38. At this time, the inlet portion 56a of the endoscope fixing portion 56 is spread by elastically deformation, so that the fitting portion 66 is engaged in the vicinity of the forceps plug 63, and the inlet portion 56a thereof is fixed at a predetermined portion while fitting it to the outer surface of the cylindrical portion 38.

Subsequently, the guide wire 2 protruding from the forceps plug 63 is inserted into the distal end 6a of the guide lumen 6 of the tube sheath 16, and projected from the inlet opening 32 of the guide lumen by inserting the same into the interior of the guide lumen 6. In this state, the U-shaped portion 37 of the first connection portion 26 of the papilotomy knife 1 is attached to the cylindrical adapter portion 60 of the adapter 23 while elastically deforming the U-shaped portion 37.

At this time, the fixing portion 42 is inserted from the opening end 40A of the engaging portion 40, and is fitted to the bottom portion 40B until it is brought into contact with the bottom portion 40B while elastically deforming the projection portions 41. As depicted in FIG. 1, the fixing portion 42 is held and engaged at the engaging portion 40, and the second operating portion 22 is connected to the first operating portion 21.

Also, the first connection portion 26 is caused to slide on the first cylindrical portion 38 so that the forceps plug 63 and the guide lumen inlet opening 32 of the guide wire insertion portion 32 are roughly positioned on the same straight line and face each other, and the forceps plug 63 and the guide lumen inlet opening 32 are disposed with 70 mm of the distance therebetween.

Figure 21:
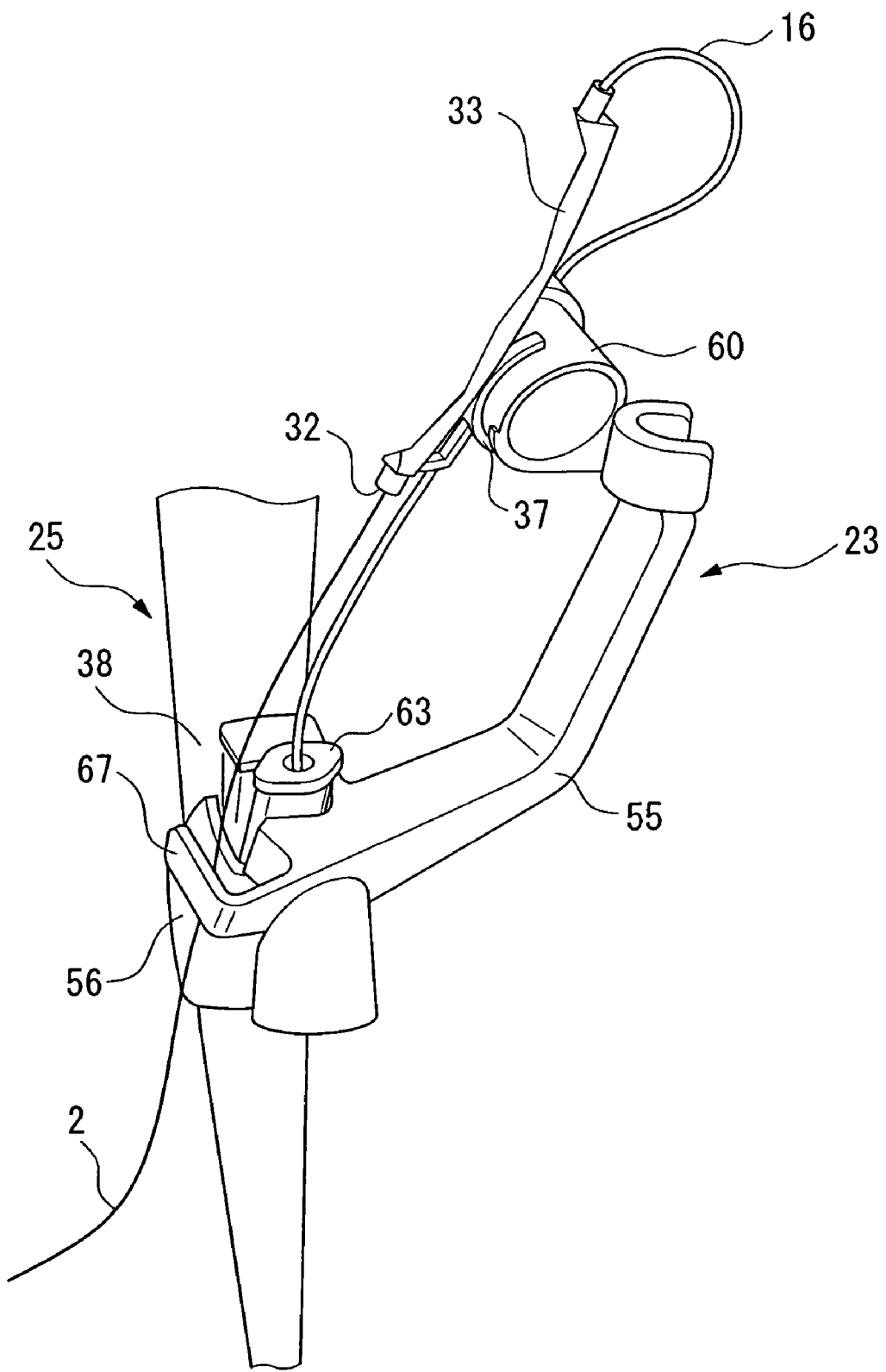
FIG. 21 is a schematic view depicting a state where the papilotomy knife according to Embodiment 1 of the invention is mounted in an endoscope.

At this time, as depicted in FIG. 21, the tube sheath 16 extending upward from the forceps plug 63 and the guide wire 2 extending downward from the guide lumen inlet opening 32 are brought into a state where the tube sheath 16 and the guide lumen inlet opening 32 are adjacent to each other and are juxtaposed in parallel roughly on the same straight line, that is, a state where an operator can hold both with a single hand.

Accordingly, when inserting and removing the tube sheath 16 in the channel 5, such an operation is enabled in which an operator holds the operating portion 25 of the endoscope 3 with one hand, and holds the tube sheath 16 and the guide wire 2 with the other hand, and then sends them in the same direction with the same amount of movement.

Figure 22:
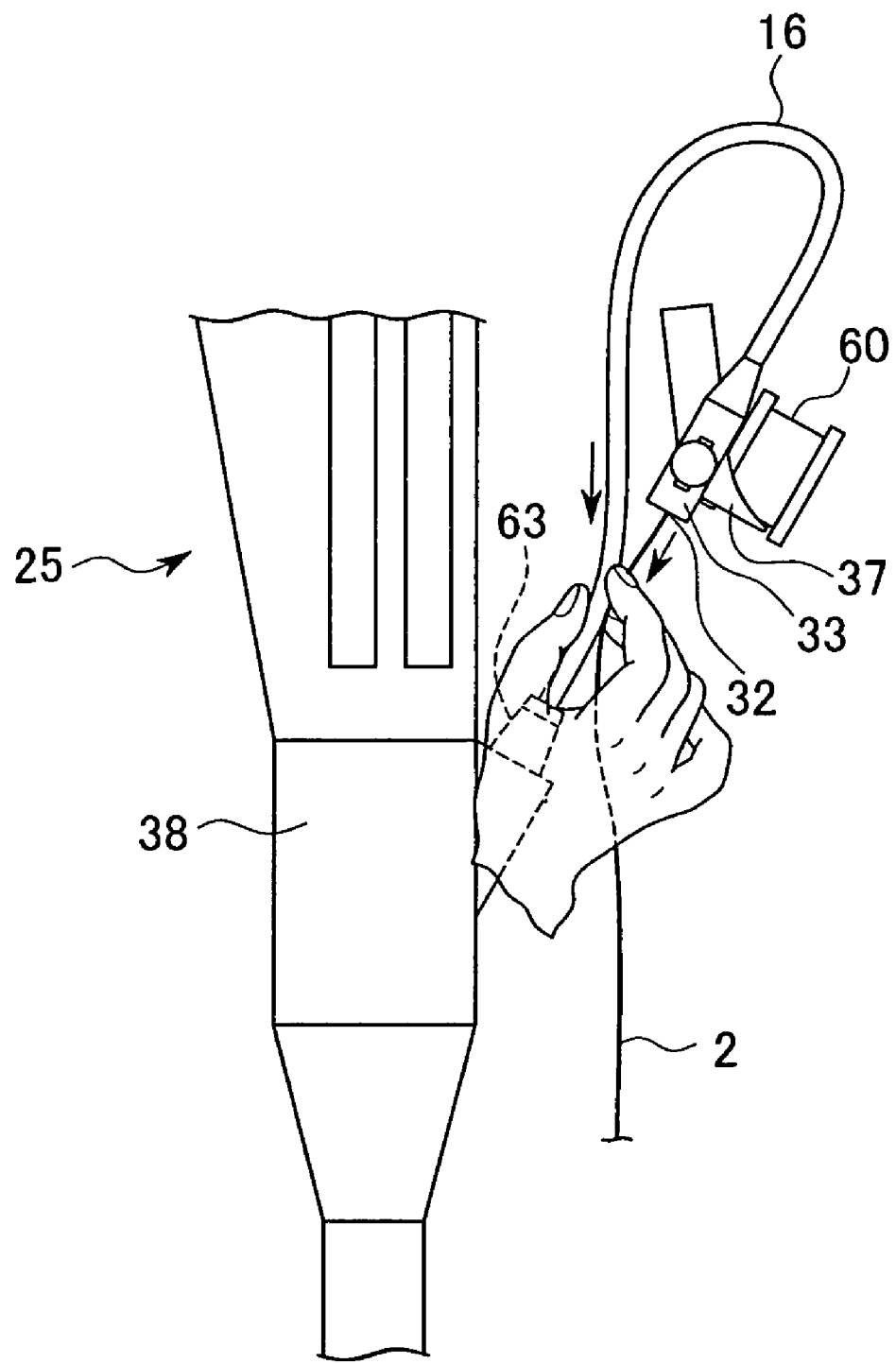
FIG. 22 is a schematic view depicting a state where the papilotomy knife according to Embodiment 1 of the invention is mounted in an endoscope.
Figure 23:
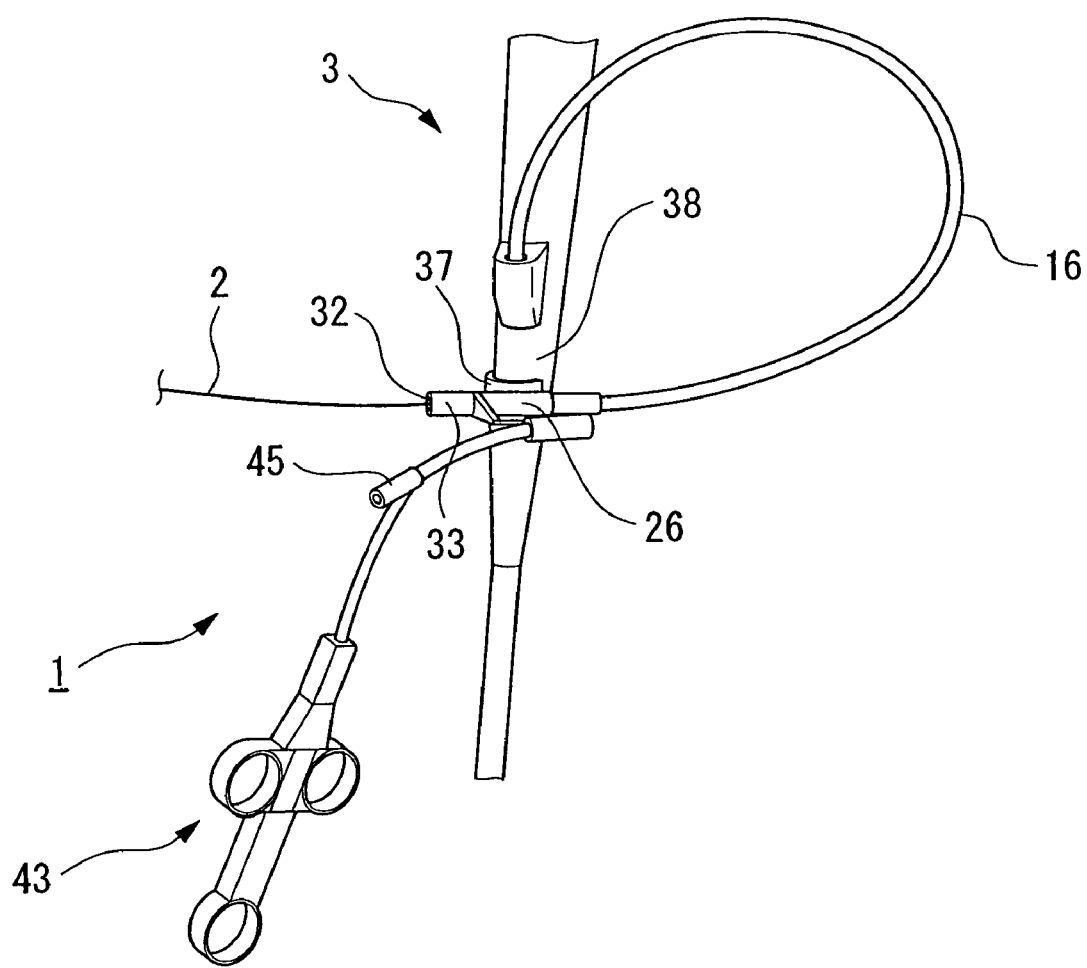
FIG. 23 is a schematic view depicting a state where the papilotomy knife according to Embodiment 1 of the invention is directly mounted in an endoscope.

When inserting the tube sheath 16 into the channel 5, as depicted in FIG. 22, the tube sheath 16 and the guide wire 2 are held with one hand, and the tube sheath 16 is moved from the forceps plug 63 in the direction of insertion of the same into the channel 5. At this time, while the tube sheath 16 is inserted, the guide wire 2 is moved in the opposite direction of the tube sheath 16 and is removed from the channel 5. At this time, the insertion length (amount of inserting movement) of the guide wire 2 in line with movement of the tube sheath 16 becomes a length equivalent to the pulling-out length (the amount of pulling-out movement) of the guide wire 2 from the guide lumen inlet opening 32. As a result, the amount of inserting movement is actually offset by the amount of pulling-out movement, wherein the relative position between the distal end portion 2a of the guide wire 2 and the distal end of the channel 5 does not move, and is kept at the same position as when the operation is commenced.

Usually, the distal end of the endoscope 3 is located at a substantially fixed position in a human body during operation. Therefore, the relative position between the distal end of the endoscope 3 and the distal end portion 2a of the guide wire 2 is kept at a fixed position in the human body.

Accordingly, work normally carried out by two skilled persons, which is for making the amount of pulling-out movement and the amount of inserting movement identical to each other, can be easily and reliably carried out by a lone operator. Therefore, it becomes possible to easily and quickly insert the tube sheath 16 with the guide wire 2 remaining in the channel 5.

Figure 5:
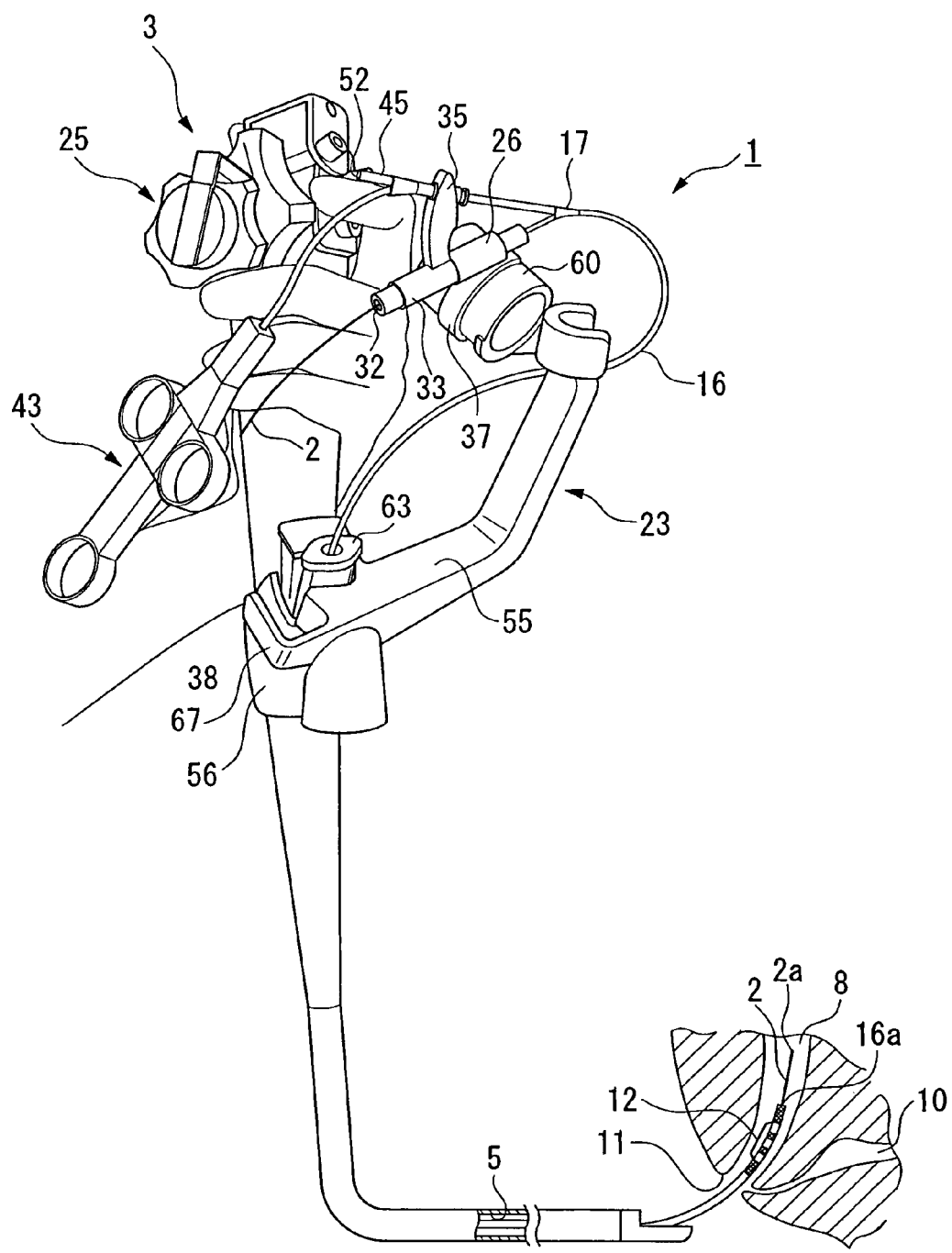
FIG. 5 is a schematic view depicting a state where the papilotomy knife according to Embodiment 1 of the invention is used in combination with an endoscope.

Thus, the inserting operation is stopped at the time when the distal end 16a of the tube sheath 16 protrudes from the distal end of the endoscope 3 to a desired length. Subsequently, the U-shaped portion 37 is turned by roughly 90 degrees with respect to the cylindrical adapter portion 60 to change the directions of the first operating portion 25 and the second operating portion 25. As depicted in FIG. 5, the state where the guide lumen inlet opening 32 and the forceps plug 63 are opposed to each other comes to an end. Also, the terminal portion 47 of the knife operation handle 43 is connected to a high-frequency power source (not shown), and then the inserting work is carried out.

When carrying out a treatment using the knife portion 12, X-ray are radiated, and the position of the knife portion 12 is checked using a contrasting chip 31.

Next, a syringe having a contrasting medium (not shown) therein is attached to the fluid-feeding mouthpiece 52. The contrasting medium is supplied into the fluid-feeding lumen 7 and is fed out through the distal end 7a. High-frequency power is supplied from a high-frequency power source while checking the position of the knife portion 12, and the slide portion 48 is slid with respect to the operation main body 50 and a predetermined incising treatment is carried out by operating the knife portion 12.

At this time, where there is an assistant, the assistant is caused to carry out a fluid-feeding operation and an incising operation under the instructions of the operator. In this case, the fixing portion 42 is detached from the engaging portion 40 to separate the second operating portion 22 from the first operating portion 21. Then, only the second operating portion 22 is handed to the assistant, who is caused to execute the above operations.

When the papilotomy knife 1 is removed from the channel 5 after the operation is finished, the U-shaped portion 37 is slid on the cylindrical adapter portion 60, and is again located at the position where the guide lumen inlet opening 32 and the forceps plug 63 are opposed to each other. Also, as described above, the tube sheath 16 protruding from the forceps plug 63 is made roughly parallel to the guide wire 2 protruding from the guide lumen inlet opening 32.

In this state, by operating the tube sheath 16 and the guide wire 2 to move reciprocally in the opposite direction, the tube sheath 16 can be removed from the channel 5 by the same action.

The papilotomy knife 1 is bifurcated into the first tube sheath 18 and the second tube sheath 20 at the bifurcated portion 17. Therefore, by separating the second operating portion 22 from the first operating portion 21 in a state where the first operating portion 21 is connected to the cylindrical portion 38 of the endoscope 3 via the first connection portion 26, an operator who operates the endoscope 3 can operate the first operating portion 21, and an assistant who is located apart from the operator can operate the second operating portion 22.

In addition, since the engaging portion 40 is disposed so that the center axis C3 forms an angle of 22 degrees to the center axis C2 of the guide wire insertion portion 33 at the position apart by 45 mm or more from the center axis C2 of the guide wire insertion portion 33, it is possible to sufficiently secure an operation area in which reciprocally movement operation of the guide wire 2 are carried out, even in a state where the fixing portion 42 is held at and engaged with the engaging portion 40, and operation can be easily carried out.

At this time, it is possible to prevent the fixing portion 42 from dropping off from the engaging portion 40 during treatment and to engage them together using the projection portion 41 of the engaging portion 40. Also, since the engaging portion 40 has the above-described structure, it is possible to mold the engaging portion 40 by pressing the production dies from both the opening end 40A side and the bottom portion 40B side when producing the same, so that moldability can be improved.

Furthermore, since the wire tube sheath 46 is made of a flexible material, it is possible to turn the knife operation handle 43 in a direction along which operation can be facilitated.

In addition, when the fixing portion 42 is separated from the engaging portion 40, the amount of protrusion of the projection portion 41 of the engaging portion 40 and the opening width of the opening ends 40A are set so that the amount of fixing force required when the fixing portion 42 is held at and engaged with the engaging portion 40 is made smaller than the amount of fixing force required when the U-shaped portion 37 is attached to the cylindrical adapter portion 60 of the adapter 23. Therefore, it is possible to prevent the U-shaped portion 37 from disjointing the cylindrical adapter portion 60 by mistake when detaching the fixing portion 42 from the engaging portion 40, and the second operating portion 22 can be handed to an assistant.

Also, since marking is provided which identifies that the fixing portion 42 and the engaging portion 40 can be mounted to each other, it is possible to mount both of them without any mistake.

Further, since the length from the bifurcated portion 17 of the first tube sheath 18 to the attaching position of the first connection portion 26 is 250 mm or more, it is possible to bend the first tube sheath 18 at a sufficiently large curvature ratio when the first connection portion 26 is fixed at the cylindrical adapter portion 60 of the adapter 23, and it is possible to reduce the sliding resistance between the guide wire 2 and the first tube sheath 18 when reciprocally movement operation of the guide wire 2 is carried out.

At this time, since the connection portion of the first tube sheath 18 with the guide wire insertion portion 33 is covered by a reinforcement tube sheath 16 for preventing them from being folded, it is possible to prevent bending of the first tube sheath 18 hindering insertion of the guide wire 2.

Still further, since the distance between the proximal end of the bifurcated portion 17 and the distal end of the operation main body 50 is set to a length of 410 mm, at which the distance between the operator and the assistant is made adequate, a sufficient distance can be secured between the operator and the assistant by separating the first operating portion 21 from the second operating portion 22 when the operator and the assistant simultaneously operate, so that smooth operation can be carried out.

In addition, since the length between the distal end of the tube sheath 16 and the bifurcated portion 17 is set to 1700 mm or more, it is possible to project the distal end 16a of the tube sheath 16 by a length of 200 mm from the channel 5 with the tube sheath 16 inserted into the channel 5 when the distance of 1400 mm that is a length from the forceps plug 63 to the distal end of the channel 5 is taken into consideration. Usually, since the length at which an instrument can be inserted into a bile duct is approximately 200 mm at maximum, the length can be made a sufficient protrusion length enable to the carrying out of treatment. At this time, it is possible to set a length of 100 mm from the forceps plug 63 to the U-shaped portion 37, and a sufficient length to enable carrying out of insertion and pulling-out operations with respect to the tube sheath 16 and the guide wire 2 can be secured, and at the same time, it becomes possible to easily insert and pull out the tube sheath 16 when replacing the same.

Also, since the first connection portion 26 is disposed at a position spaced by 30 to 45 mm from the guide lumen inlet opening 32, it is possible to set a length of approximately 100 mm between the guide lumen inlet opening 32 and the forceps plug 63 when the first connection portion 26 is mounted at the cylindrical adapter portion 60 of the adapter 23, and reciprocally movement operation of the guide wire 2 can be easily carried out. In addition, it is possible to set the distance between the guide lumen inlet opening 32 and the forceps plug 63 to 55 to 70 mm in a state where the guide lumen inlet opening 32 is opposed to the forceps plug 63. Therefore, when simultaneously carrying out an operation of inserting the guide wire 2 into the guide lumen inlet opening 32 by the same length while pulling out the tube sheath 16 from the forceps plug 63, bending of the flexible guide wire 2 is prevented, and it is possible to easily insert the guide wire 2 into the guide lumen inlet opening 32.

Figure 24:
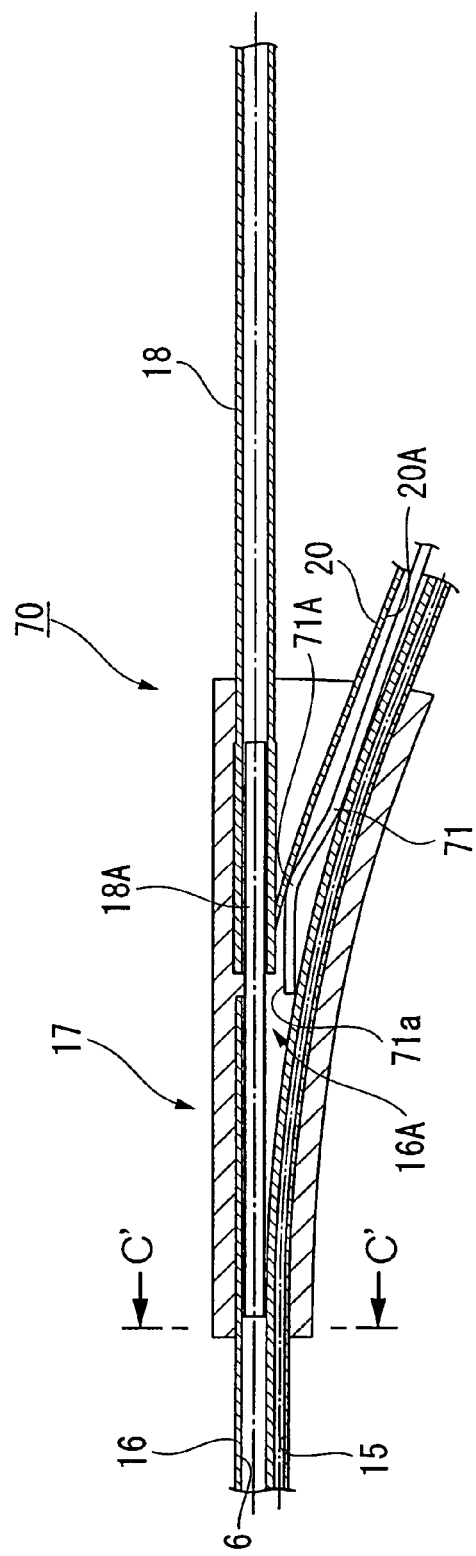
FIG. 24 is a cross-sectional view (cross-sectional view taken along the line C-C of FIG. 25) depicting a bifurcated portion of a papilotomy knife according to Embodiment 2 of the invention.
Figure 25:
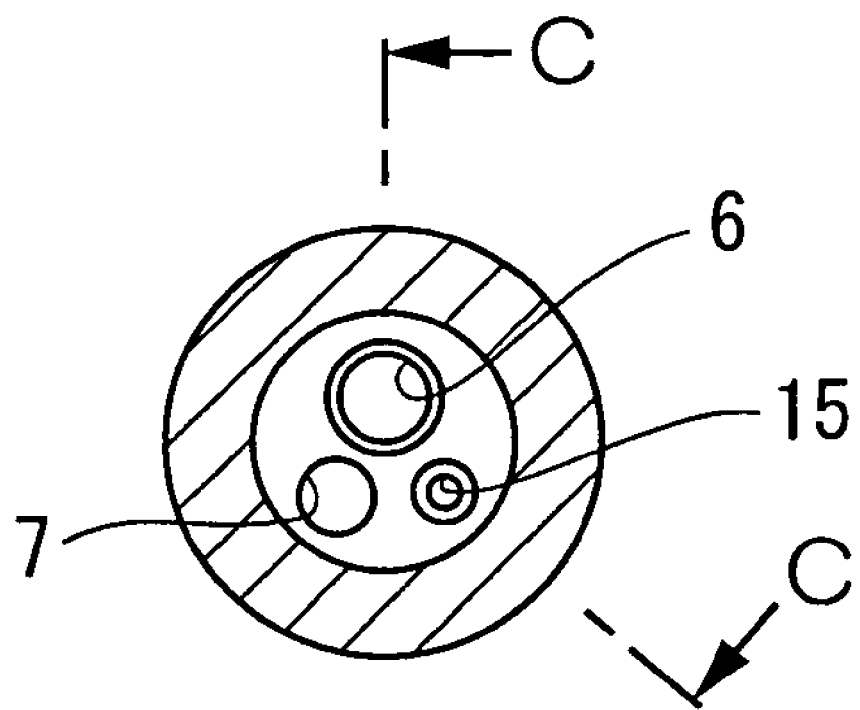
FIG. 25 is a sectional view taken along the line C'-C' of FIG. 24.

Next, a description is given of Embodiment 2 with reference to FIG. 24 and FIG. 25. Also, components of Embodiment 2 which are similar to those of Embodiment 1 described above are given the same reference numerals, and descriptions thereof are omitted.

Embodiment 2 differs from Embodiment 1 in that a papilotomy knife 70 according to Embodiment 2 is provided with a reinforcement member 71 inserted into the insertion hole 20A.

As depicted in FIG. 24 and FIG. 25, the reinforcement member 71 is provided to make the rigidity of the second tube sheath 20, which is inserted into the insertion hole 20A, and the rigidity of the first tube sheath 18, through which the guide wire 2 is inserted, roughly equivalent to each other. The reinforcement member 71 is made of stainless steel and is formed to be like a wire whose diameter is 0.3 mm.

One end 71a of the reinforcement member 71 is disposed in the notch 16A of the bifurcated portion 17. A folding portion 71A is formed at one end 71a of the reinforcement member 71. One end 71a of the reinforcement member 71 is supported by the insertion hole 20A due to a part of the folding portion 71A being brought into contact with the inner wall surface of the insertion hole 20A. Although the other end of the reinforcement member 71 is not shown, it is extended to the vicinity of the knife operation handle 43.

According to the papilotomy knife 70, actions and effects that are similar to those of the papilotomy knife according to Embodiment 1 can be brought about.

In particular, since the reinforcement member 71 is disposed in the insertion hole 20A, the rigidity at the distal end side of the tube sheath 16 is made roughly equivalent to the rigidity of the first tube sheath 18 and the second tube sheath 20, which is disposed on the proximal end, when the guide wire 2 is inserted into the guide lumen 6.

Therefore, the slide portion 48 is slid with respect to the operation main body 50 in this state, and the wire portion 13 is moved reciprocally in the wire lumen 15. Also, even if the distal end of the tube sheath 16 is bent to the knife portion 12 side, the wire lumen 15 is caused to secure sufficient rigidity that the wire lumen 15 is not collapsed over the entire length thereof. Accordingly, a predetermined treatment can be carried out while preventing deformation of the wire lumen 15.

Above description was given of preferred embodiments of the invention. However, the invention is not limited to the above-described embodiments. The invention may be subjected to addition, omission, replacement in the construction, and various modifications within the scope not departing from the spirit of the invention. Also, the invention is not limited by the above description, but is limited only by the claims attached hereto.

For example, in the above embodiments; although the first operating portion 21 is fixed at the cylindrical portion 38 of the endoscope 3 via the adapter 23, the U-shaped portion 37 of the first operating portion 21 may be directly mounted at the cylindrical portion 38 of the endoscope 3 without using the adapter 23.

In addition, although the papilotomy knife 1 is employed as an instrument, any instrument may be employed as long as it is an instrument having a slender hollow body, such as a balloon, which is inserted into the channel 5 and pulled out therefrom by relatively moving the hollow body with the wire guide remaining therein after inserting the guide wire into the interior of the hollow body.

Further, the first operating portion 21 may not be detachably attached to the first connection portion 26, but may be detachably attached to the second operating portion 22.

According to the instrument for an endoscope of the present invention, since the proximal end of the sheath portion is bifurcated into the first sheath portion and the second sheath portion, for example, it is possible for an operator, who operates the endoscope, to operate the proximal end of the first sheath portion and for an assistant, who stands apart from the operator, to operate the proximal end of the second sheath portion by separating the first sheath portion and the second sheath portion from each other. This is the same where the first sheath portion is operated by the assistant and the second sheath portion is operated by the operator.

In addition, it is possible for a lone operator or assistant to operate an instrument by holding the first sheath portion and the second sheath portion.

In the instrument for an endoscope, for example, since it is possible to mount the first operating portion, which is to be operated by an operator, in an endoscope, the first operating portion is mounted, in advance, in the endoscope by the operator except when necessity dictates otherwise. Therefore, it is not necessary for the operator to hold the first operating portion at all times, wherein the operator can concentrate on operating the endoscope. Further, since the second operating portion can be mounted at the first operating portion, it is possible a lone the operator to carry out all operations by mounting the first operating portion in the endoscope and mounting the second operating portion in the first operating portion. Also, the first operating portion may be mounted in the second operating portion with the second operating portion mounted in the endoscope.

In the instrument for an endoscope, when the guide wire is inserted into the guide lumen, the rigidity at the distal end side of the sheath portion becomes roughly the same as that at the proximal end side thereof. Therefore, even if the second operating portion is operated in this state, the distal end portion of the instrument can be operated without collapse of the lumen.

According to the instrument for an endoscope of the present invention, it is possible to perform the operations of an operator and an assistant separately, and adequate treatment operation can be efficiently carried out in a short time.

An instrument for an endoscope according to the invention is an instrument for an endoscope which is able to move reciprocally in the channel of the endoscope along a guide wire, including a sheath portion having a guide lumen into which the guide wire is inserted and another lumen disposed along the guide lumen, wherein the proximal end of the sheath portion is bifurcated into the first sheath portion having the guide lumen and the second sheath portion having another lumen. With the instrument for an endoscope according to the invention, it is possible to perform the operations of an operator and the operation of an assistant separately, and an adequate treatment operation can be efficiently carried out in a short time.

What is claimed is:

1. An instrument for an endoscope, which is able to move reciprocally in a channel of the endoscope along a guide wire, comprising;
    a sheath portion having a guide lumen into which the guide wire is inserted and another lumen disposed along the guide lumen, the proximal end of the sheath portion being bifurcated into a first sheath portion having the guide lumen and a second sheath portion having the another lumen;
    an instrument distal end portion for carrying out treatment on a portion to be treated, connected to the distal end of the sheath portion;
    a first operating portion for inserting and pulling out the guide wire, connected to the proximal end of the first sheath portion;
    a second operating portion for operating the instrument distal end portion, connected to the proximal end of the second sheath portion; and
    a second connection portion provided on the first operating portion, and which allows the second operating portion to detachably engage and disengage with the first operating portion; wherein
    one end of the second connection portion is fixed to the first operating portion,
    the second operating portion is attachable to and detachable from another end of the second connection portion fixed to the first operating portion; and
    when the second operating portion is attached to the first operating portion via the second connection portion, a center axis of the first sheath portion connected to the first operating portion and a center axis of the second sheath portion connected to the second operating portion are maintained at a predetermined angle and predetermined distance with respect to each other, the predetermined angle being an acute angle.

2. The instrument for an endoscope according to claim 1, further comprising a first connection portion provided on the first operating portion, and which allows the first operating portion to detachably engage and disengage with the endoscope.

3. The instrument for an endo scope according to claim 1, further comprising a reinforcement portion for maintaining the rigidity of the second sheath portion roughly at the same rigidity as that of the first sheath portion in which the guide wire is inserted into the guide lumen, inserted into an insertion hole disposed in the second sheath portion along another lumen.

4. The instrument for an endoscope according to claim 2, wherein the first connection portion has a U-shaped portion which is allowed to detachably engage and disengage with the endoscope.

5. The instrument for an endoscope according to claim 1, wherein the predetermined angle is substantially 22 degrees.

6. The instrument for an endoscope according to claim 1, wherein the second operating portion is adjacent to the first operating portion.

7. An operating method for the instrument for an endoscope, the instrument being able to move reciprocally in a channel of the endoscope along a guide wire, and being provided with:
- a sheath portion having a guide lumen into which the guide wire is inserted and another lumen disposed along the guide lumen, the proximal end of the sheath portion being bifurcated into a first sheath portion having the guide lumen and a second sheath portion having the another lumen;
- an instrument distal end portion for carrying out treatment on a portion to be treated, connected to the distal end of the sheath portion;
- a first operating portion for inserting and pulling out the guide wire, connected to the proximal end of the first sheath portion;
- a second operating portion for operating the instrument distal end portion, connected to the proximal end of the second sheath portion; and
- a second connection portion provided on the first operating portion, and which allows the second operating portion to detachably engage and disengage with the first operating portion; wherein the first and second operating portions being capable of being joined or separated from each other, the operating method comprising operating the first operating portion and the second operating portion attached to the first operating portion such that one operator uses the first and second operating portions, operating the first operating portion and the second operating portion separated from the first operating portion such that two operators respectively use the first and second operating portions, and maintaining a center axis of the first sheath portion connected to the first operating portion and a center axis of the second sheath portion connected to the second operating portion at a predetermined angle and predetermined distance with respect to each other, the predetermined angle being an acute angle.

* * * * *

UNITED STATES PATENT AND TRADEMARK OFFICE
CERTIFICATE OF CORRECTION

| | | |
|---|---|---|
| PATENT NO. | : 8,038,597 B2 | Page 1 of 1 |
| APPLICATION NO. | : 11/479492 | |
| DATED | : October 18, 2011 | |
| INVENTOR(S) | : Tsuyoshi Nakagawa et al. | |

It is certified that error appears in the above-identified patent and that said Letters Patent is hereby corrected as shown below:

Title Page, Item (73) should read:

(73) Assignee: Olympus Medical Systems Corp., Tokyo (JP)
Olympus Corporation, Tokyo (JP)

Signed and Sealed this
Tenth Day of January, 2012

David J. Kappos
*Director of the United States Patent and Trademark Office*